US00PP16371P2

(12) United States Plant Patent
Davasse

(10) Patent No.: US PP16,371 P2
(45) Date of Patent: Mar. 21, 2006

(54) ***PHYSOCARPUS* PLANT NAMED 'MINDIA'**

(50) Latin Name: *Physocarpus opulifolius*
Varietal Denomination: Mindia

(75) Inventor: Jean-Paul Davasse, Angers (FR)

(73) Assignee: Spring Meadow Nursery, Inc., Grand Haven, MI (US)

( * ) Notice: Subject to any disclaimer, the term of this patent is extended or adjusted under 35 U.S.C. 154(b) by 21 days.

(21) Appl. No.: 10/968,808

(22) Filed: Oct. 19, 2004

(51) Int. Cl.
*A01H 5/00* (2006.01)

(52) U.S. Cl. ..... Plt./226

(58) Field of Classification Search ..... Plt./226
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Physocarpus* plant named 'Mindia', characterized by its upright, mounding and compact plant habit; freely branching growth habit; copper-colored leaves with deep lobes and serration; and resistance to Powdery Mildew.

1 Drawing Sheet

Botanical classification/cultivar designation: *Physocarpus opulifolius* cultivar Mindia.

BACKGROUND OF THE INVENTION

The present Invention relates to a new and distinct cultivar of *Physocarpus* plant, botanically known as *Physocarpus opulifolius,* and hereinafter referred to by the name 'Mindia'.

The new *Physocarpus* is a product of a breeding program conducted by the Inventor in Angers, France. The objective of the breeding program was to create new compact and freely branching *Physocarpus* cultivars.

The new *Physocarpus* originated from a cross-pollination made by the Inventor of the *Physocarpus opulifolius* cultivar Darts Gold, not patented, as the female, or seed, parent with the *Physocarpus opulifolius* cultivar Monlo, disclosed in U.S. Plant Pat. No. 11,211, as the male, or pollen, parent. The new *Physocarpus* was discovered and selected by the Inventor during the summer of 2000 as a single plant in a controlled environment in Angers, France, within a population of the progeny resulting from the cross-pollination.

Asexual reproduction of the new *Physocarpus* by cuttings was first conducted in Angers, France during the summer of 2002. Since then, asexual reproduction by cuttings has shown that the unique features of this new *Physocarpus* are stable and reproduced true to type in successive generations.

SUMMARY OF THE INVENTION

The cultivar Mindia has not been observed under all possible environmental conditions. The phenotype may vary somewhat with variations in environment such as temperature and light intensity without, however, any variance in genotype.

The following traits have been repeatedly observed and are determined to be the unique characteristics of 'Mindia'. These characteristics in combination distinguish 'Mindia' as a new and distinct *Physocarpus:*

1. Upright, mounding and compact plant habit.
2. Freely branching growth habit.

3. Copper-colored leaves with deep lobes and serration.
4. Resistant to Powdery Mildew.

Plants of the new *Physocarpus* can be compared to plants of the female parent, the cultivar Darts Gold. In side-by-side comparisons conducted in Grand Haven, Mich., plants of the new *Physocarpus* differed from plants of the cultivar Darts Gold primarily in foliage coloration as plants of the cultivar Darts Gold have gold-colored foliage.

Plants of the new *Physocarpus* are most similar to plants of the male parent, the cultivar Monlo. In side-by-side comparisons conducted in Grand Haven, Mich., plants of the new *Physocarpus* differed from plants of the cultivar Monlo in the following characteristics:

1. Plants of the new *Physocarpus* were more compact than plants of the cultivar Monlo.
2. Plants of the new *Physocarpus* were more freely branching than plants of the cultivar Monlo.
3. Plants of the new *Physocarpus* had smaller leaves than plants of the cultivar Monlo.
4. Leaves of plants of the new *Physocarpus* were copper in color whereas leaves of plants of the cultivar Monlo were purple and green in color.
5. Plants of the new *Physocarpus* were resistant to Powdery Mildew whereas plants of the cultivar Monlo were not resistant to Powdery Mildew.

Plants of the new *Physocarpus* can be compared to plants of the cultivar Diabolo, not patented. In side-by-side comparisons conducted in Grand Haven, Mich., plants of the new *Physocarpus* differed from plants of the cultivar Diabolo in the following characteristics:

1. Plants of the new *Physocarpus* were more compact than plants of the cultivar Diabolo.
2. Plants of the new *Physocarpus* were more freely branching than plants of the cultivar Diabolo.
3. Leaves of plants of the new *Physocarpus* were copper in color whereas leaves of plants of the cultivar Diabolo were green to black in color.
4. Plants of the new *Physocarpus* were resistant to Powdery Mildew whereas plants of the cultivar Diabolo were not resistant to Powdery Mildew.

BRIEF DESCRIPTION OF THE PHOTOGRAPH

The accompanying colored photograph illustrates the overall appearance of the new *Physocarpus* showing the colors as true as it is reasonably possible to obtain in colored reproductions of this type. Colors in the photograph may differ from the color values cited in the detailed botanical description which accurately describe the colors of the new *Physocarpus*. The photograph comprises a side perspective view of a typical plant of 'Mindia' grown in an outdoor nursery.

DETAILED BOTANICAL DESCRIPTION

The aforementioned photographs and following observations and measurements describe three-year old plants grown in Grand Haven, Mich., in an outdoor nursery. During the production of the plants, day temperatures ranged from −20 to 30° C. and night temperatures ranged from −20 to 20° C. Color references are made to The Royal Horticultural Society Colour Chart, 1995 edition, except where general terms of ordinary dictionary significance are used. The photographs and description were taken during the summer.

Botanical classification: *Physocarpus opulifolius* cultivar Mindia.

Parentage:

*Female, or seed, parent.*—*Physocarpus opulifolius* cultivar Darts Gold not patented.

*Male, or pollen, parent.*—*Physocarpus opulifolius* cultivar Monlo, disclosed in U.S. Plant Pat. No. 11,211.

Propagation:

*Type.*—By softwood cuttings.

*Time to initiate roots.*—About 15 days at 25° C.

*Time to produce a rooted plant.*—About 65 days at 25° C.

*Root description.*—Fine, fibrous, white in color; freely branching, dense.

Plant description:

*Appearance.*—Perennial deciduous shrub. Upright, mounding and compact plant habit; rounded inverted triangle. Very freely branching; about 26 lateral branches per plant; dense and full plants. Vigorous growth habit.

*Plant height.*—About 60 cm.

*Plant width or area of spread.*—About 40 cm.

*Lateral branches.*—Length: About 54 cm. Diameter: About 4 mm. Internode length: About 4.2 cm. Strength: Strong. Texture: Glabrous, smooth. Color: 185A.

*Foliage description.*—Arrangement: Alternate; simple. Length: About 8 cm. Width: About 5.5 cm. Shape: Ovate; deeply lobed with three lobes per leaf. Apex: Acute. Base: Cordate to cuneate. Margin: Serrate to dentate. Venation pattern: Pinnate. Texture, upper and lower surfaces: Smooth, glabrous. Color: Developing foliage, upper surface: A blend of 169A and 150A; towards the margins, 183A. Developing foliage, lower surface: 145A. Fully expanded foliage, upper surface: A blend of 178B and 166A. Fully expanded foliage, lower surface: 138A. Venation, upper surface: A blend of 166A and 185A. Venation, lower surface: 194A. Petiole: Length: About 3.5 cm. Diameter: About 1.5 mm. Texture, upper and lower surfaces: Glabrous, smooth. Color, upper and lower surfaces: 185A.

Flower description:

*Appearance.*—Small single rotate flowers arranged in spherical corymbs. Flowers not persistent. Flowers not fragrant.

*Natural flowering season.*—Plants flower during June and July in Grand Haven, Mich.

*Postproduction longevity.*—Individual flowers maintain good color and substance for about two to three weeks on the plant when grown in an outdoor environment.

*Flower bud.*—Length: About 3.5 mm. Diameter: About 3 mm. Shape: Elliptic. Color: 65D.

*Corymbs.*—Diameter: About 2.5 cm. Length: About 2.5 cm. Quantity of flowers per corymb: About 23.

*Flowers.*—Diameter: About 8 mm. Height (depth): About 6 mm.

*Petals.*—Quantity per flower: Five. Length: About 4.5 mm. Width: About 4.5 mm. Shape: Elliptic to obovate. Apex: Obtuse. Base: Attenuate. Margin: Entire. Texture, upper and lower surfaces: Smooth, glabrous. Color: Developing petals, upper surface: 155D. Developing petals, lower surface: 65C. Fully expanded petals, upper and lower surfaces: 155D; color becoming close to 197C with development.

*Sepals.*—Quantity per flower: Five. Length: About 1 mm. Width: Less than 1 mm. Shape: Subulate. Apex: Acute. Base: Obtuse. Margin: Entire. Texture, upper and lower surfaces: Smooth, glabrous. Color, upper and lower surfaces: 144A.

*Peduncles.*—Length: About 1.3 cm. Diameter: About 0.5 mm. Strength: Flexible, weak. Color: 144A.

*Reproductive organs.*—Stamens: Quantity per flower: Numerous, about 20 to 40. Anther shape: Oblong. Anther length: About 0.5 mm. Anther color: 154D. Pollen amount: Scarce. Pollen color: 154D. Pistils: Quantity per flower: About four. Pistil length: About 0.5 mm. Stigma shape: Globular. Stigma color: 145B. Style length: About 0.45 mm. Style color: 145B. Ovary color: 145D.

*Fruit/seed.*—Plants of the new *Physocarpus* have not been observed to produce fruit and seed.

Disease/pest resistance: Plants of the new *Physocarpus* have been observed to resistant to Powdery Mildew. Plants of the new *Physocarpus* have not been observed to be resistant to pests and other pathogens common to *Physocarpus*.

Temperature tolerance: Plants of the new *Physocarpus* have been observed to tolerate temperatures from about −35 to 38° C.

It is claimed:

1. A new and distinct cultivar of *Physocarpus* plant named 'Mindia', as illustrated and described.

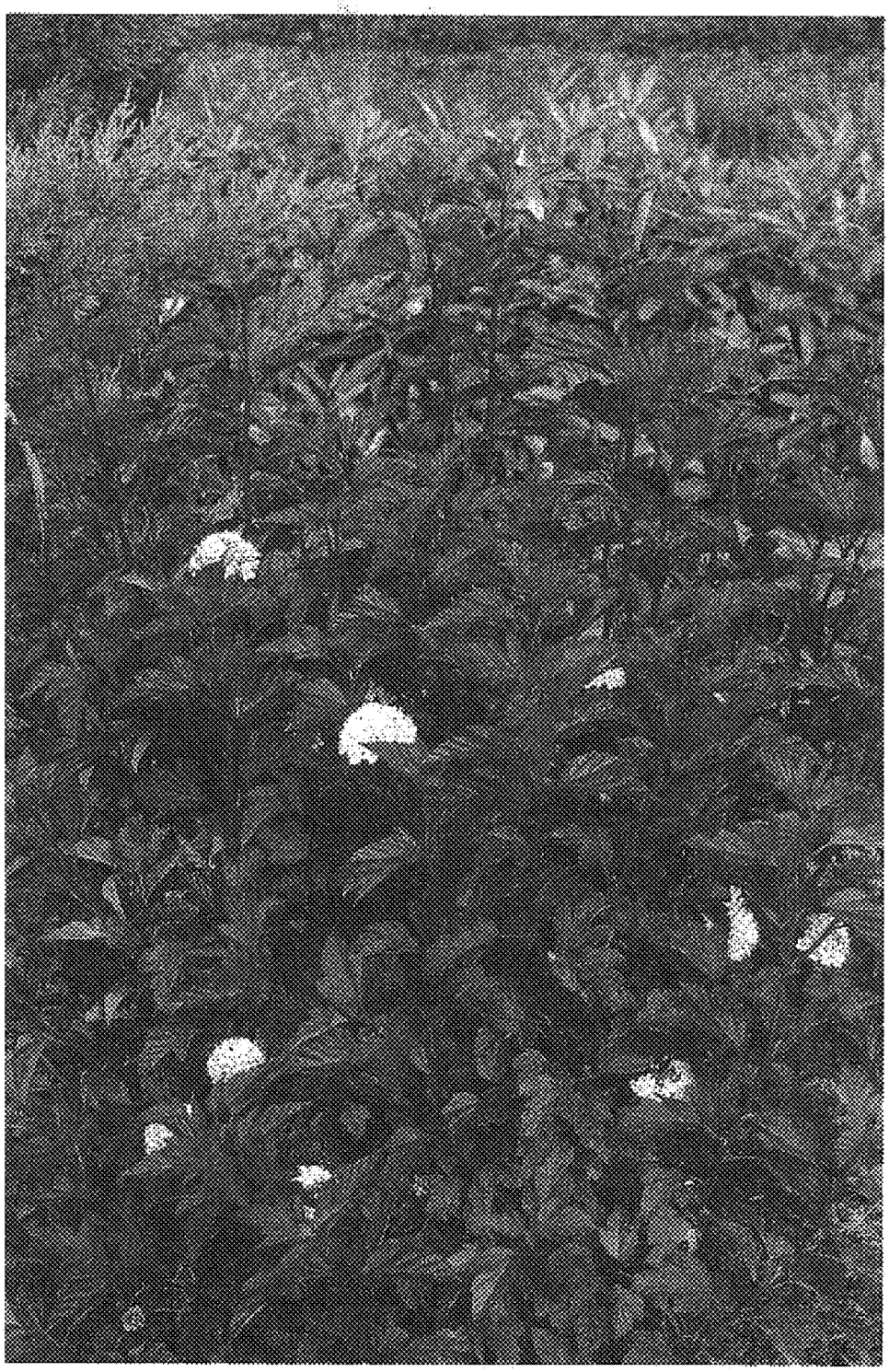

* * * * *